(12) United States Patent
Marcinkowska et al.

(10) Patent No.: US 10,197,572 B2
(45) Date of Patent: Feb. 5, 2019

(54) METHOD AND KIT FOR DETECTION OF DELTANOID-RESISTANT LEUKEMIA CELLS AND ANTIBODY FOR USE THEREIN

(71) Applicant: WROCLAWSKIE CENTRUM BADAN EIT+ SP. Z O.O., Wroclaw (PL)

(72) Inventors: Ewa Marcinkowska, Wroclaw (PL); Aleksandra Marchwicka, Wroclaw (PL); Filip Radom, Chrzanow (PL); Marta Matusiewicz, Prusy (PL); Piotr Jakimowicz, Wroclaw (PL); Filip Jelen, Wroclaw (PL); Maciej Mazurek, Wroclaw (PL)

(73) Assignee: WROCLAWSKIE CENTRUM BADAN EIT+ SP. Z O.O., Wroclaw (PL)

( * ) Notice: Subject to any disclaimer, the term of this patent is extended or adjusted under 35 U.S.C. 154(b) by 0 days.

(21) Appl. No.: 15/320,738

(22) PCT Filed: Jun. 12, 2015

(86) PCT No.: PCT/IB2015/054463
§ 371 (c)(1),
(2) Date: Dec. 20, 2016

(87) PCT Pub. No.: WO2015/193780
PCT Pub. Date: Dec. 23, 2015

(65) Prior Publication Data
US 2017/0131281 A1    May 11, 2017

(30) Foreign Application Priority Data
Jun. 20, 2014   (PL) .................................... P.408620

(51) Int. Cl.
*G01N 33/574*    (2006.01)
*G01N 33/569*    (2006.01)

(52) U.S. Cl.
CPC .. *G01N 33/57426* (2013.01); *G01N 33/56972* (2013.01); *G01N 33/57492* (2013.01); *G01N 2800/52* (2013.01)

(58) Field of Classification Search
None
See application file for complete search history.

(56) References Cited

U.S. PATENT DOCUMENTS
2010/0104577 A1    4/2010   Golde et al.

FOREIGN PATENT DOCUMENTS
WO    2015/193780 A1    12/2015

OTHER PUBLICATIONS

Studzinski et al. The rationale for deltanoids in therapy for myeloid leukemia: role of KKSR-MAPK-C/EBP pathway. J. Steroid Biochem. Mol. Biol. 91(1-2): 47, pp. 1-18, Oct. 2005.*
Gocek, Elzbieta, et al., "Opposite regulation of vitamin D receptor by ATRA in AML cells susceptible and resistant to vitamin D-induced differentiation," Journal of Steroid Biochemistry and Molecular Biology, 132 (2012) 220-226.
Marchwicka, Aleksandra, et al., "Perspectives of differentiation therapies of acute myeloid leukemia: the search for the molecular basis of patients' variable responses to 1,25-dihydroxyvitamin D and vitamin D analogs," Frontiers in Oncology, 4 (2014) 1-12.
International Search Report and Written Opininion, PCT/1132015/054463, dated Oct. 30, 2015.

* cited by examiner

*Primary Examiner* — Alana Harris Dent
(74) *Attorney, Agent, or Firm* — Arrigo, Lee, Guttman & Mouta-Bellum LLP (57) ABSTRACT

The present invention relates to a method and a kit and antibodies utilized therein, allowing to distinguish between leukemia cells resistant to and leukemia cells susceptible to differentiation induced by deltanoids.

6 Claims, 6 Drawing Sheets
Specification includes a Sequence Listing.

Legend:   black line – isotype control
shaded area – control cells
medium-grey line – 1nM calcitriol
dark-grey line – 10nM calcitriol
light-grey line – 100nM calcitriol

Fig. 4a

Legend: black line – isotype control
shaded area – control cells
medium-grey line – 1nM compound
dark-grey line – 10nM compound
light-grey line – 100nM compound

Fig. 4b

Legend: shaded area – cells labeled with the 8F/FITC protein
black line – cells labeled with the 6B/FITC protein

Fig. 5

6B
EVQLLESGGGLVQPGGSLRLSCAASGFTFSSYGMSWVRQAPGKGLEWVSTIRTAGRATEYADSVKGRFTISRDNS
KNTLYLQMNSLRAEDTAVYYCAKSPQTFDYWGQGTLVTVSSGGGGSGGGGSGGGGSTDIQMTQSPSSLSASVGDR
VTITCRASQSISSYLNWYQQKPGKAPKLLIYRASRLQSGVPSRFSGSGSGTDFTLTISSLQPEDFATYYCQQRLT
IPITFGQGTKVEIKRAAA

8F
EVQLLESGGGLVQPGGSLRLSCAASGFTFSSYGMSWVRQAPGKGLEWVSWIDASGTRTQYADSVKGRFTISRDNS
KNTLYLQMNSLRAEDTAVYYCAKLFRSFDYWGQGTLVTVSSGGGGSGGGGSGGGGSTDIQMTQSPSSLSASVGDR
VTITCRASQSISSYLNWYQQKPGKAPKLLIYRASSLQSGVPSRFSGSGSGTDFTLTISSLQPEDFATYYCQQGQT
LPITFGQGTKVEIKRAAA

Fig. 6

SEQUENCE LISTING

<160> NUMBER OF SEQ ID NOS: 2

<210> SEQ ID NO 1
<211> LENGTH: 243
<212> TYPE: PRT
<213> ORGANISM: artificial
<220> FEATURE:
<223> OTHER INFORMATION: antibody 6B

<400> SEQUENCE: 1

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ser Thr Ile Arg Thr Ala Gly Arg Ala Thr Glu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Pro Gln Thr Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Thr Asp Ile Gln Met Thr Gln Ser Pro Ser Ser Leu Ser
    130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Arg Ala Ser Arg Leu Gln Ser Gly Val Pro Ser
            180                 185                 190

Arg Phe Ser Gly Ser Gly Ser Gly Thr Asp Phe Thr Leu Thr Ile Ser
        195                 200                 205
```

```
Ser Leu Gln Pro Glu Asp Phe Ala Thr Tyr Tyr Cys Gln Gln Arg Leu
    210                 215                 220

Thr Ile Pro Ile Thr Phe Gly Gln Gly Thr Lys Val Glu Ile Lys Arg
225                 230                 235                 240

Ala Ala Ala

<210> SEQ ID NO 2
<211> LENGTH: 243
<212> TYPE: PRT
<213> ORGANISM: artificial
<220> FEATURE:
<223> OTHER INFORMATION: antibody 8F

<400> SEQUENCE: 2

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ser Trp Ile Asp Ala Ser Gly Thr Arg Thr Gln Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Phe Arg Ser Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Thr Asp Ile Gln Met Thr Gln Ser Pro Ser Ser Leu Ser
    130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Arg Ala Ser Ser Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Gly Gln
    210                 215                 220

Thr Leu Pro Ile Thr Phe Gly Gln Gly Thr Lys Val Glu Ile Lys Arg
225                 230                 235                 240

Ala Ala Ala
```

METHOD AND KIT FOR DETECTION OF DELTANOID-RESISTANT LEUKEMIA CELLS AND ANTIBODY FOR USE THEREIN

The present invention relates to a method and a kit allowing to distinguish between leukemia cells resistant to, and leukemia cells susceptible to differentiation mediated by deltanoids. More particularly, the invention is associated with use of proteins interacting with antigens present on the surface of acute myeloid leukemia cells and enabling identification of susceptible cells by distinguishing these from the cells resistant to deltanoid therapy.

Myeloid leukemias are a heterogenic group of diseases characterized by increased numbers of cancer cells derived from the hematopoietic system in blood, bone marrow and other tissues. Acute Myeloid Leukemias (AML) are rare in children, but the risk of morbidity increases with age. AMLs usually have severe clinical course. Currently, the average survival rate of persons after diagnosing the disease is 10-16 months. The incidence of AML is approximately 3.7 per 100,000 persons within one year and is higher in men than in women (4.6 versus 3.0). It increases with age; before 65 years it is 1.9 and after reaching 65 years it rises to 18.6. Within the last 10 years, a significant increase in AML morbidity was reported, associated with lifetime prolongation. The AMLs may be of a primary nature, with the cause unknown, or of a secondary nature, when they develop from an existing myelodysplasia or as a result of receiving anti-cancer drugs. Numerous disease subtypes may be identified, depending on genetic changes, morphological, immunophenotypic and cytochemical features. Depending on the type of acute myeloid leukemia different forms of therapy are employed, which is why the identification of the actual leukemia type is very important. The probability of achieving complete remission is influenced by a number of factors, such as illness duration and applying a correct and efficient therapy [Meir Wetzler et al. Acute and chronic myeloid leukemia, 104, p. 738, part 6, Oncology and Haematology; Hoffbrand, Moss and Pettit, 2006: Essential Haematology. Blackwell Publishing]. The only effective targeted therapy in the current AML treatment is the therapy with retinoic acid, in the all-trans form (ATRA), used in case of the M3 subtype AML. The ATRA therapy in combination with arsenic trioxide provides two years survival in 97% patients [Lo-Coco F et al. Retinoic acid and arsenic trioxide for acute promyelocytic leukemia. N Engl J Med, 2013 369: p. 111-21]. The most important feature characterizing this type of therapy is the induction of differentiation of leukemia cells.

It is currently known that the active form of vitamin $D_3$ (calcitriol) and its analogs may be useful in treating leukemias, inter alia causing inhibition of proliferation and induction of differentiation [Ma, Y. et al., Vitamin D and acute myeloid leukemia. Journal of Cancer, 2010. 3: p. 101-107; Gocek, E. and E. Marcinkowska, Differentiation therapy of acute myeloid leukemia. Cancers, 2011. 3: p. 2402-2420].

However, no method has been disclosed up to date that would allow to distinguish between the lines susceptible and resistant to drug using antibodies directed against a surface antigen.

In light of the above, it is very important to find proteins interacting with antigens present on the surface of leukemia cells, that would allow to distinguish the cells resistant to differentiation mediated by deltanoids (namely calcitriol and analogs thereof) from the cells susceptible to differentiation mediated by deltanoids.

There is a large need in the field for a diagnostic kit that would provide rapid information on the susceptibility of the patient suffering from acute myeloid leukemia to deltanoid therapy.

The present invention provides a solution to this problem, enabling a quick evaluation of patient's cells susceptibility to the planned therapy and significantly, enabling an accelerated selection of the correct and individually matched treatment method.

The object of the invention is a method of detecting deltanoid-resistant leukemia cells, characterized by the fact that antigen is detected in vitro on the surface of isolated examined leukemia cells and the cells having the antigen detected on their surface are considered resistant to deltanoid therapy, wherein antibody comprising SEQ ID NO: 1 is used for the detection.

Preferably, in the method according to the invention antibody with a sequence comprising SEQ ID NO: 2 is used as a negative control.

Preferably, flow cytometry is used for analysis.

Preferably, an ELISA-type assay is used for analysis.

A further object of the invention is an antibody for detection of deltanoid-resistant leukemia cells, comprising the sequence of SEQ ID NO: 1.

Preferably, the antibody according to the invention is obtained by a phage display method.

A further object of the invention is an antibody comprising the sequence of SEQ ID NO: 2, used as a negative control in the method according to the invention.

Preferably, the above mentioned antibody is obtained by a phage display method.

Another object of the invention is a use of an antibody comprising the sequence of SEQ ID NO: 1 for detection of leukemia cells resistant to therapy with deltanoids.

Another object of the invention is a kit for detection of leukemia cells resistant to therapy with deltanoids, the kit comprising an antibody comprising the sequence of SEQ ID NO: 1, being specific against an antigen present on the surface of the studied leukemia cells.

Preferably, the kit according to the invention comprises an antibody with a sequence comprising SEQ ID NO: 2 as a negative control.

More particularly, the method according to the invention allows to distinguish between cell lines sensitive and insensitive to a drug, based on antibodies in an scFv format, obtained by a phage display method.

Therefore, the object of the invention are amino acid sequences of antibodies in an scFv format, specifically distinguishing the KG1 line from the HL60 line, as well as a method of selection of antibodies in an scFv format on whole cells, which enabled to obtain the antibodies.

In order to obtain scFv fragments distinguishing insensitive cells from drug-sensitive cells, the hereinafter described Tomlinson library was utilized.

The selection was conducted using two libraries: Tomlinson I and Tomlinson J [Tomlinson, I. and J. Tomlinson. [cit. 2014; available at: www.lifesciences.sourcebioscience.com]. Both libraries were created on the basis of a human antibody variable region (scFv). The scFv molecule consist of a single variable heavy chain and a variable light chain, linked by a flexible linker, enabling re-folding thereof and formation of a functional $F_v$ domain.

Mutations were introduced at 18 positions of the hypervariable regions—at locations responsible for antigen binding. This generates considerable diversity for each library ($10^8$ variants). The difference between both libraries lies in the type of changes introduced within the hypervariable region. In one of them, changes of the (AGT)(AGC)T type were introduced in the codons, allowing to obtain N, T, S, D, A G, Y, C amino acid residues. In the other library, changes allowing to obtain all 20 amino acids were introduced.

A selection round, according to the library creators' principles, involves incubation of the library with an antigen and recovery of phage particles with the displayed scFv having bound (in case of positive selection) or not having bound (negative selection) the antigen. Such phages are then propagated in bacteria and isolated as a starting material for next selection round. Enrichment of the library with antigen-recognizing clones allows to enhance their competitiveness in subsequent selection rounds, and as a result to isolate the clones with the strongest binding to target antigens.

After screening the library and finding the positively interacting clones, transformation of non-suppressor bacteria with the selected clone plasmids is performed, allowing to obtain scFvs not being fused with a phage envelope protein, secreted to the culture medium. The expressed scFvs may be purified on a protein A resin or on columns of the HisTrap type. The obtained antibody in an scFv format has a molecular mass of approx. 28 kDa and contains two tags: His-tag and c-myc.

In several patents and publications, a selection method employing whole cells was used, utilizing various types of phage display libraries [Hagay, Y. et al., Specific human antibodies for selective cancer therapy, B.-T.G.I. Ltd., Editor. 2006; Dong, J., A novel peptide selected from phage display library of random peptides, can efficiently target into human breast cancer cell. Chin. Sci. Bullet., 2008. 53: p. 860-867; Wang, F. et al. Selection of CC chemokine receptor 5-binding peptide from a phage display peptide library. Biosci Biotechnol Biochem, 2006. 70(9): p. 2035-41; Lee, S. et al., Targeting bladder tumor cells in vivo and in the urine with a peptide identified by phage display. Mol Cancer Res, 2007. 5(1): p. 11-9; Witt, H. et al., Identification of a rhabdomyosarcoma targeting peptide by phage display with sequence similarities to the tumour lymphatic-homing peptide LyP-1. Int J Cancer, 2009. 124(9): p. 2026-32].

The method according to the invention differs in principles and practice from the hitherto used methods, since it allows to distinguish the cells not on the basis of protein overexpression or according to the criteria for healthy—diseased cells but on the basis of the criteria for drug-susceptible—drug-resistant cells.

In one patented solution [Hagay, Y. et al., Specific human antibodies for selective cancer therapy, B.-T.G.I. Ltd., Editor. 2006] a phage display selection on whole cells was performed. The fundamental difference between the previous experiments and the disclosed method is the use of two independent cell lines. The aim is to obtain antibodies capable of distinguishing a 'naturally' drug-sensitive line from a 'naturally' insensitive line. Counter-selection was not done choosing immature, excited or known antigen overexpressing cells as in the methods known in the prior art.

In the Lee, S. et al., Targeting bladder tumor cells in vivo and in the urine with a peptide identified by phage display. Mol Cancer Res, 2007. 5(1): p. 11-9 publication, a method was proposed for distinguishing between healthy and cancerous cells by performing counter-selection for healthy cells. This is however a method designed for different purposes, namely for imaging cancerous lesions in patients. The method according to the invention is intended inter alia for the analysis of susceptibility of patient's cells to a particular therapy.

Similarly as in the case of Hagaya et al. patent [Zella, L. et al., Multifunctional enhancers regulate mouse and human vitamin D receptor gene transcription. Mol Endocrinol, 2010. 24: p. 128-47], in the Wang et al. experiment from 2006 [Wang, F. et al., Selection of CC chemokine receptor 5-binding peptide from a phage display peptide library. Biosci Biotechnol Biochem, 2006. 70(9): p. 2035-41] cells overexpressing CCR5 were used. Additionally, washing to remove unbound phages was done by centrifugation in Eppendorf-type tubes, while in the method used according to the invention mild centrifugation of a 96-well plate was used, allowing a substantial acceleration of the procedure and a possibility of testing various conditions in one, swift approach (method optimization).

Figure 6:
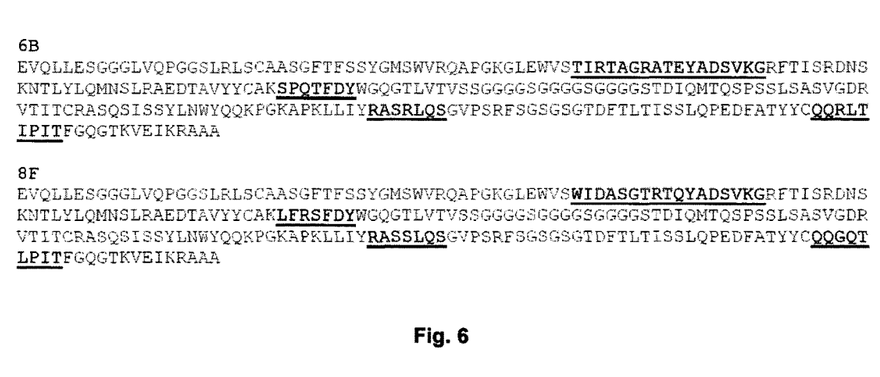
FIG. 6 shows the sequences of antibodies with indicated (underlined) hypervariable regions.

In publications from 2008-2009 [Dong, J., A novel peptide selected from phage display library of random peptides, can efficiently target into human breast cancer cell. Chin. Sci. Bullet., 2008. 53: p. 860-867; Witt, H. et al., Identification of a rhabdomyosarcoma targeting peptide by phage display with sequence similarities to the tumour lymphatic-homing peptide LyP-1. Int J Cancer, 2009. 124(9): p. 2026-32] selection was conducted on whole cells in culture but only internalized phages were isolated. In the present invention, the focus is on the phages that have been bound to the cell surface and have not been internalized. This allowed to select specific scFvs that remain on the surface relatively long. This is an advantageous property in diagnostic tests, such as ELISA or flow cytometry. Sequences of the obtained antibodies are shown on FIG. 6 together with characteristic elements thereof indicated.

The object of the invention in embodiments thereof is illustrated on drawings wherein

FIGS. 2 and 3 show a shift (a change in fluorescence intensity) of the KG1 and HL60 cells after labeling with KG1-specific 6B antibody in the form of dot plots (dot-blot) presenting all events and the indicated HL60/KG1 population. The selected populations were then analyzed for FITC labeling and data was presented on histograms.

FIGS. 4 and 5 show a verification of susceptibility or resistance to differentiation mediated by deltanoids and the evidence for the correlation of the resistance to differentiation mediated by deltanoids with the expression of the 6B protein binding surface antigen;

According to the invention, cells from the KG1 acute myeloid leukemia line were used as a model for cells resistant to differentiation mediated by deltanoids. It is known from scientific literature and the inventor's own experience that these cells are not susceptible to differentiation mediated by even the most active deltanoids [Munker, R. et al., Vitamin D compounds. Effect on clonal proliferation and differentiation of human myeloid cells. J Clin Invest, 1986. 78: p. 424-30; Gocek, E. et al., Opposite regulation of vitamin D receptor by ATRA in AML cells susceptible and resistant to vitamin D-induced differentiation. J Steroid Biochem Mol Biol, 2012. 132(3-5): p. 220-6]. The HL60 acute myeloid leukemia cell line, used in laboratories engaged in studying deltanoid-mediated differentiation, served as a sensitive line model [Marcinkowska, E. et al., Cell differentiating and anti-proliferative activity of side-chain modified analogs of 1,25-dihydroxyvitamin D3. J Steroid Biochem Mol Biol, 1998. 67(1): p. 71-8; Gallagher, R. et al., Characterization of the continuous, differentiating myeloid cell line (HL-60) from a patient with acute promyelocytic leukemia. Blood, 1979. 54: p. 713-733; Brackman, D. et al., Expression of cell surface antigens during the differentiation of HL-60 cells induced by 1,25-dihydroxyvitamin D3, retinoic acid and DMSO. Leuk Res, 1995. 19: p. 57-64].

Figure 4A:
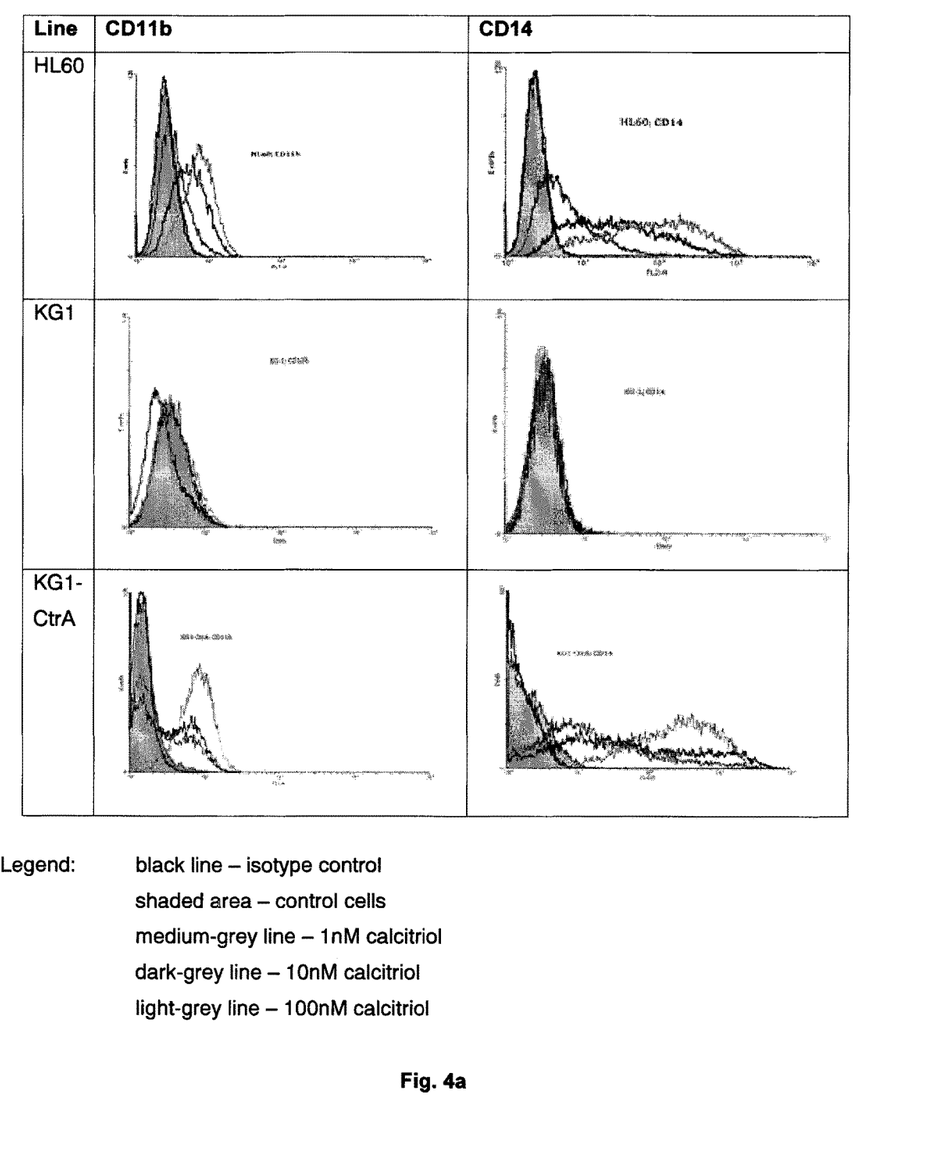
FIG. 4*a* shows an assay of the expression of differentiation antigens after exposure of HL60, KG1 and KG1-CtrA cells lines to calcitriol.
Figure 4B:
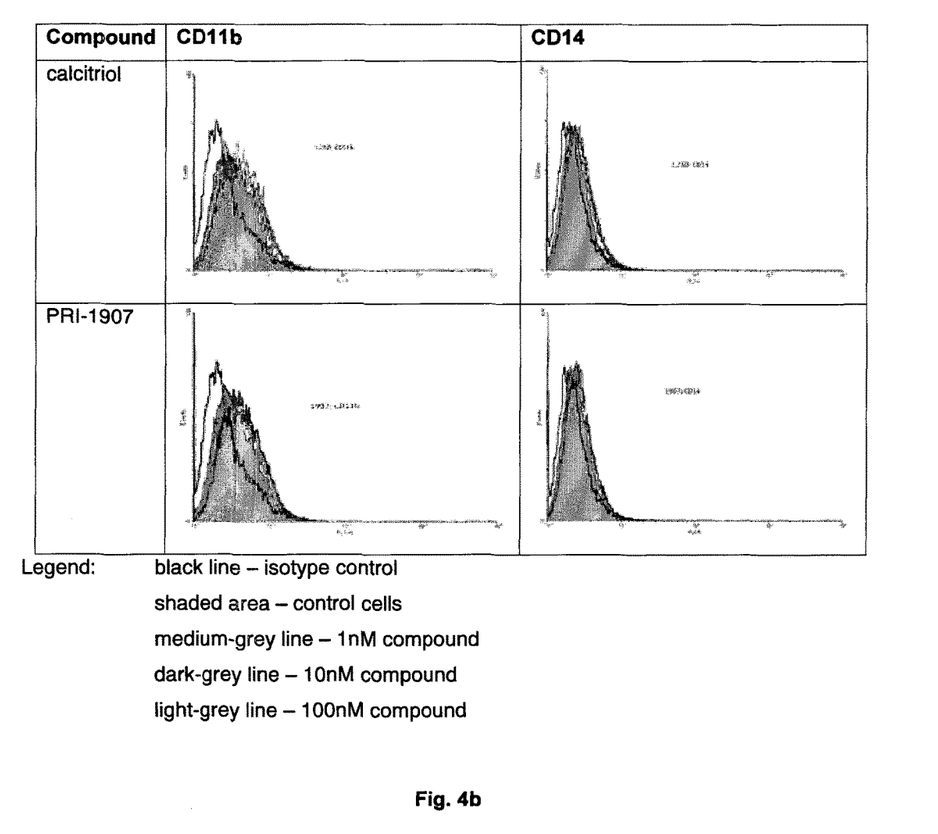
FIG. 4*b* shows an assay of the expression of differentiation antigens after exposure of KG1 cells lines to calcitriol or a PRI-1907 analog.

Studying susceptibility to differentiation mediated by deltanoids is done in a number of ways. One of these is observing the appearance of antigens typical for macrophages on the surface of deltanoid (calcitriol or analogs) treated cells, serving important functions for the macrophages. Such surface antigens are inter alia CD14 (bacterial lipopolysaccharide receptor [Da Silva Correia, J, Soldau, K, Christen, U, Tobias, P S, Ulevitch, R J Lipopolysaccharide is in close proximity to each of the proteins in its membrane receptor complex. transfer from CD14 to TLR4 and MD-2. J Biol Chem, 2001. 276: 21129-21135.]) or CD11b proteins ($\alpha_M\beta_2$-integrin subunit [Carlos, T M, Harlan, J M. Leukocyte-endothelial adhesion molecules. Blood, 1994. 84: 2068-2101]). The HL60 cells after exposure even to low concentrations of calcitriol or analogs thereof significantly increase expression of these antigens, while the KG1 cells, even after exposure to high concentrations of these compounds, do not alter CD11 b and CD14 expression [Gocek, E. et al., Opposite regulation of vitamin D receptor by ATRA in AML cells susceptible and resistant to vitamin D-induced differentiation. J Steroid Biochem Mol Biol, 2012. 132(3-5): p. 220-6]. The inventors performed genetic modification of the KG1 line, transfecting it with the Control A plasmid (CtrA; Santa Cruz), which restored susceptibility to differentiation for the cells. The KG1-CtrA cells after exposure to calcitriol or active analogs significantly increase expression of differentiation antigens CD11 b and CD14 (unpublished data). FIG. 4 shows exemplary histograms from flow cytometry, which demonstrate the expression of differentiation antigens on the HL60, KG1 and KG1-CtrA cells without and after exposure to calcitriol (FIG. 4a) and the lack of differentiation after exposure of KG1 cells to calcitriol or to the more active of the analogs (PRI-1907) (FIG. 4b).

Figure 5:
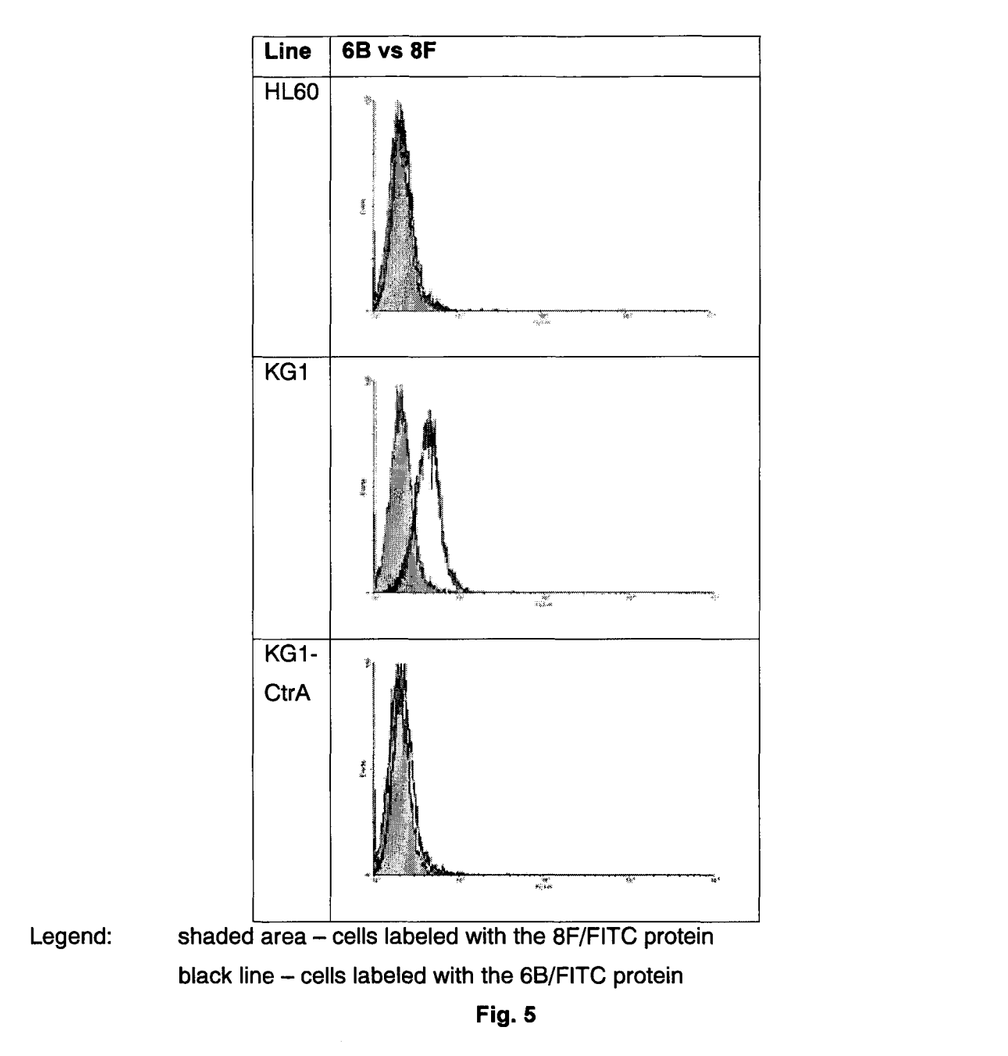
FIG. 5 shows an assay of binding of the 6B and 8F proteins to the HL60, KG-1 and KG1-CtrA cells.

FITC-labeled 6B and 8F antibodies were used to label the HL60, KG1 and KG1-CtrA cells. To this end, $5 \times 10^5$ cells of each were suspended in 50 µl of PBS buffer without calcium and magnesium ions with 0.1% BSA. Either 1 µg of the 8F/FITC protein or 1 µg of the 6B/FITC protein were added to each suspension. Samples were incubated for 45 minutes in darkness on ice, then washed with PBS without calcium and magnesium ions, supplemented with 0.1% BSA and subsequently fluorescence of the samples was read by flow cytometry. FIG. 5 shows exemplary histograms. A significant indication suggesting a connection between the 6B-binding antigen and resistance to deltanoids is the fact that this antigen is lost in KG1-CtrA cells, in which susceptibility to deltanoids was restored by genetic modification.

Since the aim of the study was to find proteins that would interact with surface antigens present on the cells, the selection of phage-displayed scFvs was conducted in the presence of whole intact cells. A feature distinguishing this invention among others is the fact that in the selection process intact cells were treated as the solid phase. It was important for the cells not to be damaged during the selection process since then the selection could proceed in respect of proteins present inside the cells.

Furthermore, the aim was to select antibodies interacting with surface antigens distinguishing the cells resistant to differentiation mediated by deltanoids from sensitive cells, so the whole selection process was conducted by a differential method, i.e. all phages displaying proteins interacting with HL60 cells surface antigens were rejected and the phages displaying proteins interacting with KG1 cells surface antigens were selected.

So far, selections with counter-selection were performed for the cells that e.g. overexpress the receptor of interest (counter-selection for the cells with natural antigen expression levels), cancerous cells (counter-selection for healthy cells). The present approach is based on the sensitivity to deltanoids of both lines. Selection on cells insensitive to the drug with counter-selection on sensitive cells allows to distinguish between them, potentially due to the protein involved in the drug-resistance mechanism. This antibody may serve to identify the receptor or the protein responsible for deltanoid resistance.

The KG1 and HL60 cells were cultured in RPMI-1640 medium+10% FBS+2 mM L-glutamine+100 units/ml penicillin+100 µg/ml streptomycin. The culture was maintained at exponential growth phase.

Five rounds of selection were performed, using positive (for KG1 line cells) and negative selection (HL60 cells) interchangeably. After each selection round the selected material was amplified.

It was particularly important to suitably propagate the material after negative selection, before it was transferred to KG1 cells. Since both lines are of myeloid origin they can exhibit great similarities in surface antigen expression which may lead to recovery of small amount of phages after negative selection. In order to effectively select clones positive for KG1, the library recovered after negative selection must be propagated first.

Selection was performed on a 96-well plate. A suitable number of cells was added to wells coated with 3% BSA and then incubated with the phage library for a defined time. After incubation the cells were washed with a buffer at physiological pH with the addition of non-ionic detergents (0.1% Tween-20), in order to remove non-specifically bound phages. The washings involved incubating the cells with the buffer, mild (130×g, 6 min) centrifugation of the 96-well plate (which protects against cellular breakdown and release of intracellular proteins including internalized scFv) and removal of the supernatant. It was decided not to attach the cells to the plate to retain the natural structure of surface antigens. For the same reasons, the plate was blocked with a 3% BSA solution beforehand. The selection scheme is shown in Table 1.

TABLE 1

Summary of consecutive selection rounds for antibodies

| Number of cells/well | Incubation time with the libraries, conditions | Number of washings (Buffer with detergent + buffer without detergent) | Bound phages elution method |
|---|---|---|---|
| Round 1: Positive selection (KG1) | | | |
| $5 \times 10^4$ | 60 min, 18° C. (mixing every 20 min) | 0 + 5 | Elution with trypsin and EDTA |
| Round 2: Negative selection (HL60) | | | |
| $1 \times 10^5$ | 60 min, 4° C. (mixing every 20 min) | 0 + 0 (cells were centrifuged, unbound phages were used to infect bacteria | Not applicable |
| Round 3: Positive selection (KG1) | | | |
| $5 \times 10^4$ | 60 min, 18° C. (mixing every 20 min) | 0 + 5 | Elution with trypsin and EDTA |
| Round 4: Negative selection (HL60) | | | |
| $1 \times 10^5$ | 60 min, 4° C. (mixing every 20 min) | 0 + 0 (cells were centrifuged, unbound phages were used to infect bacteria) | Not applicable |
| Round 5: Positive selection (KG1) | | | |
| $2.5 \times 10^4$ | 30 min, 18° C. (mixing every 15 min) | 5 + 5 | Elution with trypsin and EDTA |

With each round of positive selection the stringency of selection conditions was increased (decreasing number of cells, shortening incubation time of the library with the cells, increasing number of washings), so as to obtain antibodies with the strongest binding with the KG1 cells. Changes in phage titer after each selection round are summarized in Table 2.

TABLE 2

Changes in phage titer observed after each selection round

| library | Tomlinson I | Tomlinson J |
|---|---|---|
| round 1 (KG1) | $2.9 \times 10^5$ | $5.4 \times 10^6$ |
| round 2 (HL60) unbound | $1.1 \times 10^9$ | $1.0 \times 10^9$ |
| round 2 (HL60) bound | $1.9 \times 10^6$ | $1.2 \times 10^7$ |
| round 3 (KG1) | $1.8 \times 10^5$ | $1.2 \times 10^6$ |
| round 4 (HL60) unbound | $3.3 \times 10^9$ | $4 \times 10^9$ |
| round 4 (HL60) bound | $5 \times 10^7$ | $8.5 \times 10^7$ |
| round 5 (KG1) | $1.8 \times 10^8$ | $3.9 \times 10^7$ |

Initially, a selection approach based on centrifugation in Eppendorf- or Falcon-type tubes was attempted, like in the methods proposed previously [Wang, F. et al., Selection of CC chemokine receptor 5-binding peptide from a phage display peptide library. Biosci Biotechnol Biochem, 2006. 70(9): p. 2035-41]. However, it was found to be ineffective and time consuming. Conditions for selection on a 96-well plate were successfully optimized, substantially accelerating the selection procedure, allowing to screen a larger part of the library in shorter time.

Two methods of eluting cell-bound phages were tested. The cells were divided into two portions and eluted for 8 min with 500 mM NaCl, 100 mM glycine, pH 2.5 or with 1 mg/ml trypsin with EDTA in 37° C. Eluates were neutralized with ½ volume of 1 M Tris-HCl pH 8.0 and PBS buffer respectively. Test results are shown in Table 3. It was decided to use elution with trypsin in the actual selection.

TABLE 3

Optimization of bound phages elution method

| Library | Elution method | Titer [cfu] |
|---|---|---|
| Tomlinson I | 1 mg/ml trypsin, 0.12% EDTA | $9.5 \times 10^7$ |
| | 500 mM NaCl, 100 mM gycine, pH 2.5 | $1.5 \times 10^7$ |
| Tomlinson J | 1 mg/ml trypsin, 0.12% EDTA | $5 \times 10^8$ |
| | 500 mM NaCl, 100 mM glycine, pH 2.5 | $2.5 \times 10^8$ |

Figure 1:
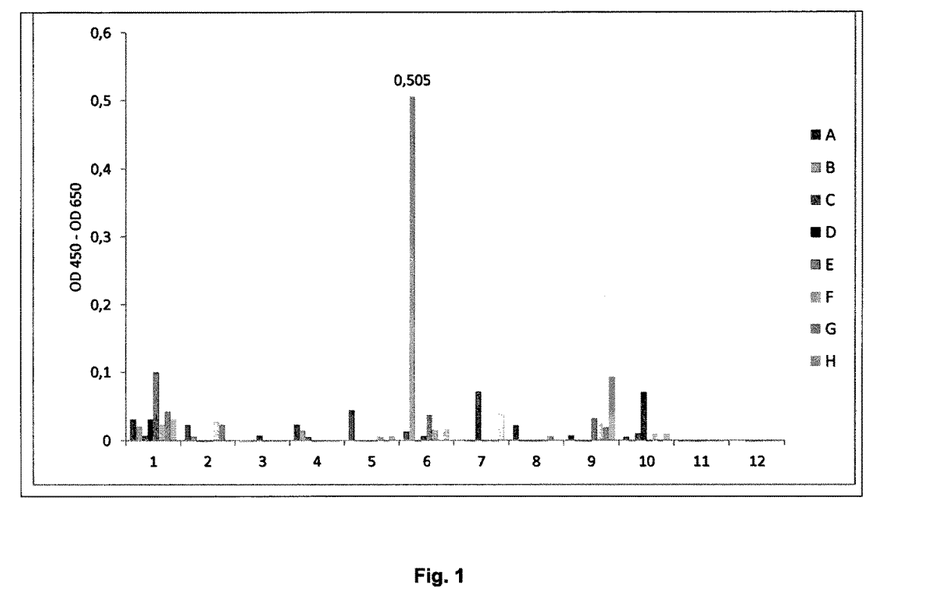
FIG. 1 shows the results of library screening with the ELISA method. The $OD_{450}$-$OD_{650}$ signal informs of the binding strength of the tested antibody to KG1 cells (more particularly: of the amount of the antibody bound to the antigen, being then recognized by a secondary HRP-conjugated antibody). Background signal, namely $OD_{450}$-$OD_{650}$ for the control with only the secondary antibody, was then subtracted from all measurements. The numbers and letters indicate the position on a 96-well plate. The signal derived from the 6B antibody is clearly prominent.

Screening the library in order to find antibodies in an scFv format, specifically interacting with the KG1 line, was done based on ELISA according to the Tomlinson protocol (phages with envelope protein fused with scFv after expression on a 96-well plate served as the primary antibody for ELISA). Again, the cells were not immobilized on a Nunc U plate but only centrifuged in mild conditions. The identified positive clones were expressed in the form of solubilized scFv (without fusion with a phage envelope protein) and purified on a protein A resin, and then tested on KG1 cells and HL60 cells obtaining desired results (specificity against KG1 line) (FIG. 1).

At the same time, it was observed that the HL60 cells spontaneously convert the substrate for HRP conjugated with the secondary antibody, giving results that need to be analyzed with caution. To this end, the reaction for HL60 was stopped sooner but the results required additional confirmation with a different method anyway. The selected antibody was tested on HL60 cells and no increased signal was reported in comparison to control with non-specific scFv.

As a result of the selection, an scFv was identified, which specifically recognizes KG1 cells line (6B), with a sequence of:

(SEQ ID NO: 1)
EVQLLESGGGLVQPGGSLRLSCAASGFTFSSYGMSWVRQAPGKGLEWVS

TIRTAGRATEYADSVKGRFTISRDNSKNTLYLQMNSLRAEDTAVYYCAK

SPQTFDYWGQGTLVTVSSGGGGSGGGGSGGGGSTDIQMTQSPSSLSASV

GDRVTITCRASQSISSYLNWYQQKPGKAPKLLIYRASRLQSGVPSRFSG

SGSGTDFTLTISSLQPEDFATYYCQQRLTIPITFGQGTKVEIKRAAA.

The proper negative control for the obtained scFv is the antibody (8F) with a sequence of:

(SEQ ID NO: 2)
EVQLLESGGGLVQPGGSLRLSCAASGFTFSSYGMSWVRQAPGKGLEWVS

WIDASGTRTQYADSVKGRFTISRDNSKNTLYLQMNSLRAEDTAVYYCAK

LFRSFDYWGQGTLVTVSSGGGGSGGGGSGGGGSTDIQMTQSPSSLSASV

GDRVTITCRASQSISSYLNWYQQKPGKAPKLLIYRASSLQSGVPSRFSG

SGSGTDFTLTISSLQPEDFATYYCQQGQTLPITFGQGTKVEIKRAAA.

This protein has an identical length as the protein displayed by the 6B clone, also having identical framework portions, differing only in hypervariable fragments of the antibody.

As a confirmation of the ELISA assays, the flow cytometry analysis was conducted, wherein the cells were labeled with a FITC-conjugated antibody in an scFv format (direct labeling) or with an antibody in an scFv format and then with a FITC-conjugated secondary antibody recognizing the former (sandwich method).

Figure 2A:
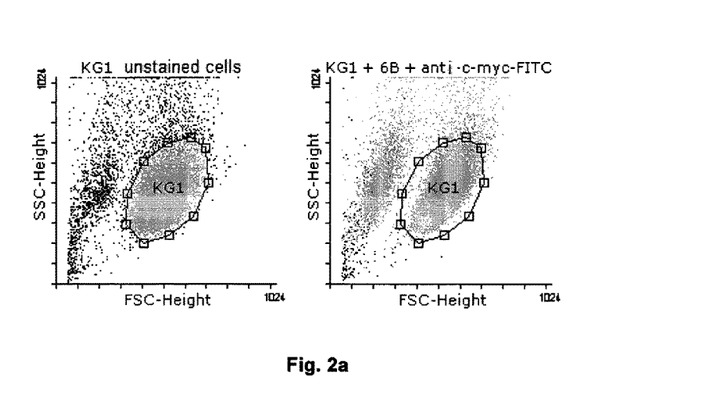
FIGS. 2*a* and 2*b* show KG1 cells labeling with the 6B protein.
Figure 2B:
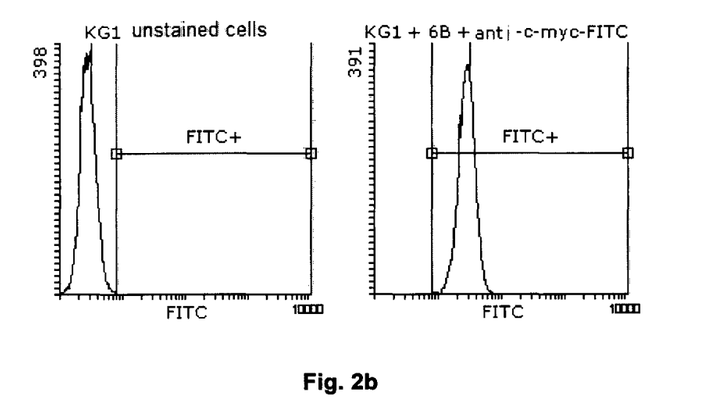
Figure 3:
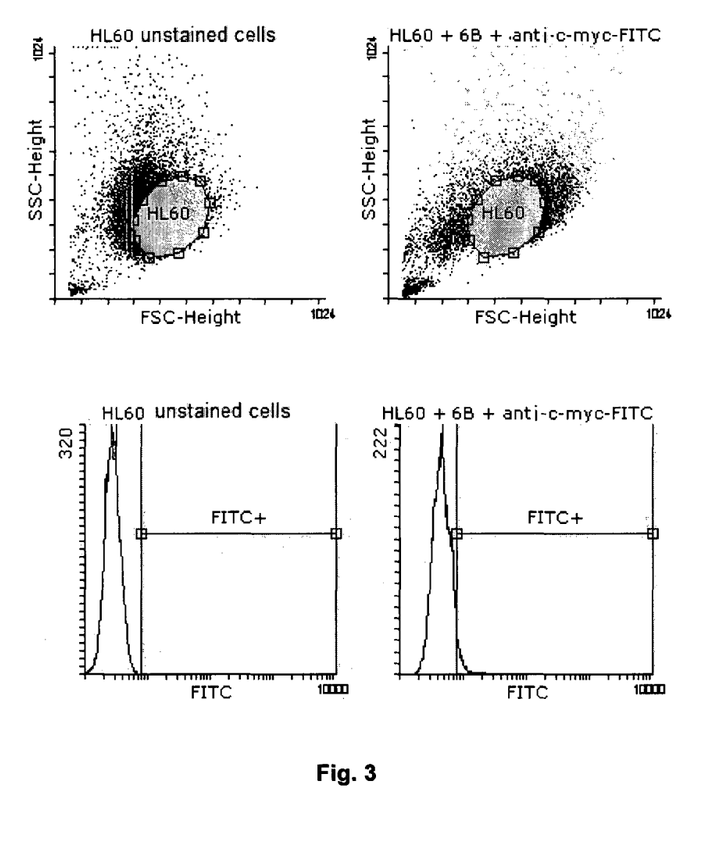
FIG. 3 shows HL60 cells labeling with the 6B protein.

A clear shift in the signal was demonstrated; almost 100% of the KG1 cells stained in the sandwich arrangement (FIG. 2) and only a few percent of the HL60 cells stained (FIG. 3), indicating high specificity of the 6B antibody (statistical summary of the obtained data is shown in Table 4).

TABLE 4

Statistical analysis of the data obtained by flow cytometry

| | All events | FITC+: % Vis | FITC+: mean | FITC+: GeoMean | FITC+: median | FITC+: CV |
|---|---|---|---|---|---|---|
| KG1 unstained cells | 14444.0 | 0.0 | 0.0 | 0.0 | 0.0 | 0.0 |
| KG1 + 6B + anti-c-myc-FITC | 14098.0 | 100.0 | 29.4 | 28.1 | 28.4 | 38.1 |
| HL60 unstained cells | 11618.0 | 0.0 | 8.7 | 8.7 | 8.3 | 8.1 |
| HL60 + 6B + anti-c-myc-FITC | 8536.0 | 4.5 | 10.7 | 9.8 | 8.9 | 92.8 |

Next, FITC labeling of the selected scFvs (KG1-recognizing antibody and the negative control for FCM) was optimized, by testing molar excess of the dye in the range of 100×-1×relative to the protein (1×, 2×, 5×, 10×, 20×, 40×, 100×). Substantial excess of the dye enables efficient scFv labeling, but removal of the unbound dye from the conjugate with scFv is a problem. Dialysis and desalting on PD-10 columns proved to be ineffective. scFv solutions, without removal of the free FITC, did not allow to distinguish between both lines, since free FITC non-specifically binds with cell membranes of both HL60 and KG1 cells. Finally, a less efficient method of labeling was chosen—with molar ratio of 1:1, allowing however to avoid non-specific interactions and resulting in clear differences in fluorimetric images of both lines.

Apart from optimizing the conditions of scFv conjugation with FITC, it was also attempted to optimize the amount of scFv-FITC conjugate by testing the range of 0.02-1 mg used per $10^5$ cells. An increase in fluorescence levels was observed depending on the amount of conjugate used. The optimal amount was found to be within the range of 0.2-0.4 μg/$10^5$ cells.

Optimal dilution of the secondary antibody in the sandwich method is 1:100 or 1:50 ($10^5$ cells).

The used method is distinguished by the following innovative elements:
a) Cells from another cancerous line (insensitive to deltanoids) served as the cells for negative control, not excited nor overexpressing the surface antigen, such as in the previous experiments.
b) The target molecule was unknown, hence the selection on whole cells. The principle was to find an antibody in an scFv format that would allow to distinguish between both lines.
c) Selection was done on a 96-well plate, unbound phages were removed by centrifugation of the plate.
d) The cells were not attached to the bottom of the plate, not to alter the structure of surface antigens, washings were done as a cycle of centrifugations.
e) Mild conditions of the centrifugation protected the cells from breakdown and release of intracellular proteins and internalized phages.
f) Antibodies in an scFv format were selected, with hitherto unknown sequences, allowing to distinguish a deltanoid-insensitive line from the sensitive line.

Up to date there has been no solution allowing to distinguish cells sensitive to deltanoids from resistant cells. Due to the postulated deltanoid applications in treatment of patients with acute myeloid leukemias, a diagnostic test identifying resistant and sensitive cells makes the therapy usable as targeted therapy. It may enable determining whether a particular therapy is effective for a particular patient. Since during therapy with deltanoids, as during other cancer treatments, the plurality of side effects is a huge problem, a preliminary diagnosis allowing a proper selection of treatment method is critical. The test according to the invention is simple and quick to use, allowing recognition of cell surface antigens, can be conducted on cells isolated from patient's peripheral blood within a few hours (approx. 1.5 h for isolation of blood cells in Ficoll gradient and approx. 1.5 h for cell labeling and flow cytometry readings).

In the diagnostic test according to the invention, antibody interacting with surface antigen is used, the antigen being characteristic for the KG1 deltanoid-resistant cells and distinguishing them from the HL60 deltanoid-sensitive cells. Furthermore, it may be used for identification and further study of the surface antigen interacting therewith. Antibodies, directed against a surface protein involved in drug resistance mechanism, can be used for production of medicaments (a conjugate of a drug with an antibody) in cancer treatment. The obtained antibodies in an scFv format are suitable for diagnostics, not only employing flow cytometry but also using ELISA-type assays. Crucial for the operation of the proposed diagnostic test is the 6B antibody, interacting with KG1 cells surface antigen and not interacting with HL60 cells surface, as well as the 8F protein being a good negative control for the above described test.

Development of methodology of differential selection of proteins interacting with cell surface antigens is also highly beneficial. The established methodology of differential selection of phage-displayed proteins against surface antigens of intact cells grown in suspension can also be used for similar tasks.

Exemplary Description of the Test Procedure of Detecting Deltanoid-resistant/-sensitive Cells in a Sample Collected from a Patient
1) Collecting 5 ml of peripheral blood from a patient recently diagnosed with acute myeloid leukemia.
2) Diluting the peripheral blood with phosphate buffer (PBS) in the 1:1 ratio.
3) Layering the diluted peripheral blood on an equal volume (10 ml) of Ficoll in a centrifugation tube.
4) Centrifugation for 30 min at 400×g acceleration at room temperature.
5) Removing the top layer containing blood serum and transferring the opalescent mononuclear cell layer to a new sterile centrifugation tube.
6) Washing the mononuclear cells three times by centrifugation in PBS at 250×g acceleration for 10 min.
7) Suspending the cells at a density of $10^7$/ml in PBS without calcium and magnesium ions, containing 0.1% albumin from bovine serum (BSA).

8) Adding either 1 μg of the 8F/FITC protein (negative sample) or 1 μg of the 6B/FITC protein (the actual sample) to the 5×10⁵ cell suspensions.
9) Incubation for 45 min in darkness on ice.
10) Washing the samples twice with 0.5 ml PBS without calcium and magnesium ions, containing 0.1% BSA by centrifugation at 250×g acceleration for 3 minutes.
11) Reading the fluorescence of the cells by flow cytometry.

The Elements of the Diagnostic Test

8F/FITC protein in concentration of 1 mg/ml; 500 μl
6B/FITC protein in concentration of 1 mg/ml: 500 μl PBS without calcium and magnesium ions, supplemented with 0.1% BSA 1.5 L.

SEQUENCE LISTING

SEQ ID NO: 1
Name: Clone 6B
Description: antibody specifically recognizing cells of the KG-1 line resistant to differentiation mediated by deltanoids

EVQLLESGGGLVQPGGSLRLSCAASGFTFSSYGMSWVRQAPGKGLEWVS

TIRTAGRATEYADSVKGRFTISRDNSKNTLYLQMNSLRAEDTAVYYCAK

SPQTFDYWGQGTLVTVSSGGGGSGGGGSGGGGSTDIQMTQSPSSLSASV

GDRVTITCRASQSISSYLNWYQQKPGKAPKWYRASRLQSGVPSRFSGSG

SGTDFTLTISSLQPEDFATYYCQQRLTIPITFGQGTKVEIKRAAA

SEQ ID NO: 2
Name: Clone 8F
Description: antibody being a negative control verifying the specificity of the test, not recognizing neither deltanoid-resistant nor sensitive leukemia cells

EVQLLESGGGLVQPGGSLRLSCAASGFTFSSYGMSWVRQAPGKGLEWVS

WIDASGTRTQYADSVKGRFTISRDNSKNTLYLQMNSLRAEDTAVYYCAK

LFRSFDYWGQGTLVTVSSGGGGSGGGGSGGGGSTDIQMTQSPSSLSASV

GDRVTITCRASQSISSYLNWYQQKPGKAPKLLIYRASSLQSGVPSRFSG

SGSGTDFTLTISSLQPEDFATYYCQQGQTLPITFGQGTKVEIKRAAA

---

The invention claimed is:

1. A method of detecting deltanoid-resistant leukemia cells, comprising:
   providing isolated leukemia cells,
   contacting the isolated leukemia cells with an antibody comprising SEQ ID NO: 1, and
   measuring binding of the antibody to an antigen on the surface of the isolated leukemia cells.

2. The method according to claim 1, further comprising:
   contacting the isolated leukemia cells with an antibody comprising SEQ ID NO: 2, and
   measuring binding of the antibody to an antigen on the surface of the isolated leukemia cells,
   wherein the antibody comprising SEQ ID NO: 2 serves as a negative control.

3. The method according to claim 1, wherein binding is measured by a process comprising flow cytometry.

4. The method according to claim 1, wherein binding is measured by a process comprising an ELISA-type assay.

5. The method of claim 1, wherein binding of the antibody comprising SEQ ID NO: 1 to the antigen on the surface of the leukemia cells is detected.

6. The method of claim 5, wherein the leukemia cells bound by the antibody are resistant to therapy with deltanoids.

\* \* \* \* \*